US011129785B2

(12) United States Patent
Segawa

(10) Patent No.: US 11,129,785 B2
(45) Date of Patent: Sep. 28, 2021

(54) RINSE-OFF CLEANSING COMPOSITIONS

(71) Applicant: The Procter & Gamble Company, Cincinnati, OH (US)

(72) Inventor: Yukari Segawa, Singapore (SG)

(73) Assignee: The Procter and Gamble Company, Cincinnati, OH (US)

( * ) Notice: Subject to any disclaimer, the term of this patent is extended or adjusted under 35 U.S.C. 154(b) by 37 days.

(21) Appl. No.: 16/536,352

(22) Filed: Aug. 9, 2019

(65) Prior Publication Data

US 2020/0046623 A1    Feb. 13, 2020

Related U.S. Application Data

(60) Provisional application No. 62/717,016, filed on Aug. 10, 2018.

(51) Int. Cl.

| | |
|---|---|
| *C11D 1/10* | (2006.01) |
| *C11D 1/66* | (2006.01) |
| *C11D 1/825* | (2006.01) |
| *A61K 8/60* | (2006.01) |
| *A61K 8/34* | (2006.01) |
| *A61K 8/41* | (2006.01) |
| *A61K 8/42* | (2006.01) |
| *A61Q 19/10* | (2006.01) |
| *C11D 3/33* | (2006.01) |
| *C11D 3/22* | (2006.01) |
| *C11D 1/90* | (2006.01) |
| *C11D 1/83* | (2006.01) |

(52) U.S. Cl.
CPC .............. *A61K 8/604* (2013.01); *A61K 8/34* (2013.01); *A61K 8/416* (2013.01); *A61K 8/42* (2013.01); *A61Q 19/10* (2013.01); *C11D 1/10* (2013.01); *C11D 1/662* (2013.01); *C11D 1/83* (2013.01); *C11D 1/90* (2013.01); *C11D 3/22* (2013.01); *C11D 3/33* (2013.01); *A61K 2800/33* (2013.01); *A61K 2800/49* (2013.01); *A61K 2800/596* (2013.01)

(58) Field of Classification Search
CPC .. C11D 1/10; C11D 1/662; C11D 1/83; C11D 1/90; C11D 3/22; C11D 3/33
USPC ....... 510/119, 123, 130, 136, 137, 138, 488, 510/501
See application file for complete search history.

(56) References Cited

U.S. PATENT DOCUMENTS

| | | | |
|---|---|---|---|
| 6,703,427 B2 | 3/2004 | Schmucker | |
| 6,903,057 B1 | 6/2005 | Tsaur | |
| 9,242,124 B2 | 1/2016 | Griffin | |
| 2005/0025957 A1 | 2/2005 | Issberner et al. | |
| 2009/0130153 A1 | 5/2009 | Issberner | |
| 2009/0131542 A1 | 5/2009 | Issberner | |
| 2011/0139170 A1 | 6/2011 | Hippe | |
| 2012/0183591 A1* | 7/2012 | Dahms | A61Q 5/006 424/401 |
| 2013/0143784 A1* | 6/2013 | Rizk | A61K 8/44 510/123 |
| 2015/0011456 A1 | 1/2015 | Griffin | |
| 2015/0315123 A1 | 11/2015 | Schuch | |
| 2017/0360672 A1* | 12/2017 | Maka | A61Q 5/00 |
| 2019/0021960 A1 | 1/2019 | Dippe | |

FOREIGN PATENT DOCUMENTS

| | | |
|---|---|---|
| CN | 104688552 A | 6/2015 |
| CN | 105434232 A | 3/2016 |
| CN | 105943463 A | 9/2016 |
| CN | 105997548 A | 10/2016 |
| CN | 105997678 A | 10/2016 |
| CN | 106109308 A | 11/2016 |
| CN | 106236690 A | 12/2016 |
| CN | 106265259 A | 1/2017 |
| CN | 106333901 A | 1/2017 |
| CN | 106491380 A | 3/2017 |
| EP | 1675562 B1 | 5/2008 |
| EP | 2794830 B1 | 12/2017 |
| EP | 3220883 B1 | 7/2018 |
| EP | 3220885 B1 | 8/2018 |
| WO | WO2010069500 A1 | 6/2010 |
| WO | WO2014082854 A2 | 6/2014 |
| WO | WO2016079007 A1 | 5/2016 |
| WO | WO2016079008 A1 | 5/2016 |

OTHER PUBLICATIONS

International Search Report and Written Opinion of the International Searching Authority, PCT/US2019/045659, dated Jan. 7, 2020, 12 pages.

* cited by examiner

*Primary Examiner* — Gregory R Delcotto

(74) *Attorney, Agent, or Firm* — Alexandra S. Anoff

(57) ABSTRACT

The present invention relates to rinse-off cleansing compositions comprising a surfactant system, in which the surfactant system comprises an alkyl polyglycoside and an acyl glutamate present in specific amounts, for providing compositions that are not only mild on the skin and/or eyes that are stable especially under acidic pH conditions, but also have simpler formulations which have fewer ingredients, good rinse-off property, and preferably more cost effective.

12 Claims, No Drawings

RINSE-OFF CLEANSING COMPOSITIONS

FIELD OF THE INVENTION

The present invention relates generally to rinse-off cleansing compositions, especially suitable for personal care.

BACKGROUND OF THE INVENTION

Sulfate-based anionic surfactants generally exhibit superior cleansing and foaming properties and are thus typically used in rinse-off personal care compositions. However, such surfactants are generally known to be harsh on the skin and/or eyes. As consumers desire milder surfactants that have a neutral to acidic pH, one approach is to use salts of glutamates which are mild on skin and/or eyes and provides good rinse-off benefit. However, such milder anionic surfactants face solubility challenges and tend to precipitate under acidic pH conditions. In order to address the solubility challenges, such milder anionic surfactants can be used in combination with other surfactants (such as amphoteric surfactants) to form surfactant complexes that are more soluble and less likely to precipitate out of the solution at acidic pH, and/or with a plurality of solubilizers that function to improve the solubility of such milder anionic surfactants and reduce/prevent their precipitation. However, the resulting compositions tend to have complex surfactant systems with many ingredients at significantly increased costs, and many tend to suffer in foaming, cleansing and/or sensory performance such as rinse-off feel. Furthermore, such complex surfactant systems may cause ocular irritation due to presence of certain solubilizers or at relatively high levels of certain solubilizers. Still further, some ingredients can pose compatibility challenges, which may be especially true in more complex formulations.

There is therefore a need for products that are not only mild on the skin and/or eyes that are stable especially under acidic pH conditions and can continue to deliver benefits characteristic of the product category, but also have simpler formulations which have fewer ingredients, good rinse-off property, and preferably more cost effective.

SUMMARY OF THE INVENTION

The present invention addresses this need, at least in part, by providing a rinse-off cleansing composition that is mild on the skin and/or eyes, stable especially under acidic pH conditions and a simpler formulation with fewer ingredients, while also providing the benefits consumers come to expect, such as good-rinse off feel. One aspect of the present invention provides for a rinse-off cleansing composition comprising: from 0.5% to 40%, by total weight of said cleansing composition, of a surfactant system, the surfactant system comprising an alkyl polyglycoside and an acyl glutamate, wherein the alkyl polyglycoside and the acyl glutamate are present at more than 70% by total weight of the surfactant system, and wherein pH value of said cleansing composition is 7.5 or less.

Another aspect provides for a rinse-off cleansing composition, comprising: from 5% to 15%, by total weight of said cleansing composition, of a surfactant system, the surfactant system comprising essentially of an alkyl polyglycoside and an acyl glutamate, wherein the weight ratio of the alkyl polyglycoside to the acyl glutamate is greater than 1, and optionally substantially free of one or more solubilizers, wherein pH value of said cleansing composition is from 5 to 6.

While the specification concludes with claims that particularly point out and distinctly claim the invention, it is believed the present invention will be better understood from the following description.

DETAILED DESCRIPTION OF THE INVENTION

Definitions

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt %" herein. All molecular weights as used herein are weight average molecular weights expressed as grams/mole, unless otherwise specified.

As used herein, the articles including "a" and "an" when used in a claim, are understood to mean one or more of what is claimed or described.

As used herein, the terms "comprise", "comprises", "comprising", "include", "includes", "including", "contain", "contains", and "containing" are meant to be non-limiting, i.e., other steps and other sections which do not affect the end of result can be added. The above terms encompass the terms "consisting of" and "consisting essentially of".

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "substantially free of" refers to the presence of a stated ingredient at 3% or less, preferably 2% or less, more preferably 1% or less, still more preferably 0.1% or less by total weight of a composition. "Free of" refers to complete absence of a stated ingredient or is not present at detectable levels. However, the stated ingredient may incidentally form as a byproduct or a reaction product of the other components of the composition, or is present only as an impurity in one or more of the other ingredients deliberately included.

The term "consisting/consist(s) essentially of" as used in the definition of ingredients present in compositions of the present invention (e.g. present at more than 96%, preferably more than 97%, more preferably more than 98%, still more preferably more than 99%) is intended to exclude the presence of other materials in such amounts as to interfere substantially with the properties and characteristics possessed by the compositions set forth but to permit the presence of other materials in such amounts as not substantially to affect said properties and characteristics adversely.

As used herein, "cleansing composition" refers to compositions intended for topical application to surfaces such as skin, hair, floor, hard surface and the like. The cleansing compositions can be, for example, in the form of a liquid, semi-liquid cream, lotion, gel, or solid.

As used herein, "personal care composition" refers to compositions intended for topical application to skin and/or hair. The personal care compositions can be, for example, in the form of a liquid, semi-liquid cream, lotion, gel, or solid and are intended for topical application to the skin and/or hair. Examples of personal care compositions can include but are not limited to bar soaps, shampoos, conditioning shampoos, body or face washes, moisturizing body or face washes, shower gels, skin cleansers, cleansing milks, in shower body moisturizers, pet shampoos, shaving preparations, etc.

As used herein, "rinse-off" means the intended product usage includes application to skin and/or hair followed by rinsing and/or wiping the product from the skin and/or hair within a few seconds to minutes of the application step.

Rinse-Off Cleansing Compositions

Compositions of the present invention relates generally to rinse-off cleansing compositions, and preferably rinse-off personal care compositions.

A rinse-off cleansing composition of the present invention is preferably characterized by from 0.5% to 40%, by total weight of said cleansing composition, of a surfactant system, the surfactant system comprising an alkyl polyglycoside and an acyl glutamate, wherein the alkyl polyglycoside and the acyl glutamate are present at more than 70% by total weight of the surfactant system, and wherein pH value of said cleansing composition is 7.5 or less.

Preferably, the alkyl polyglycoside and the acyl glutamate are present at more than 80%, preferably more than 90%, more preferably more than 95%, still more preferably more than 98%, by total weight of the surfactant system, wherein preferably the surfactant system consists essentially of only the alkyl polyglycoside and the acyl glutamate.

Preferably, the cleansing composition comprises from 5% to 30%, preferably from 5% to 20%, and more preferably from 5% to 15%, alternatively from 7% to 12%, or from 8% to 10%, by total weight of said cleansing composition, of the surfactant system. Compositions of the present invention can be provided in non-concentrated forms (e.g. from 0.5% to 15%, by total weight of the composition, of the surfactant system) or in concentrated forms (e.g. from 15% to 40%, by total weight of composition, of the surfactant system).

Preferably, the pH value of said cleansing composition is no more than 7.0, more preferably no more than 6.5, still more preferably no more than 6.0, still more preferably no more than 5.5, alternatively from 5 to 6.

Preferably, the weight ratio of the alkyl polyglycoside to the acyl glutamate is from 0.1 to 9 preferably from 0.4 to 9, more preferably from 1 to 9, and most preferably from 1.5 to 9, alternatively from 1.5 to 2. It is believed, without being limited by theory, that the weight ratio of the alkyl polyglycoside to the acyl glutamate may be greater than 9 depending on the minimum amount of the acyl glutamate that is required to achieve an acceptable cleansing performance.

A preferred rinse-off cleansing composition of the prevent invention comprises from 5% to 15%, by total weight of said cleansing composition, of a surfactant system, the surfactant system comprising essentially of an alkyl polyglycoside and an acyl glutamate, wherein the weight ratio of the alkyl polyglycoside to the acyl glutamate is greater than 1, and optionally substantially free of one or more solubilizers, wherein pH value of said cleansing composition is from 5 to 6.

Surfactant System

Alkyl Polyglycoside (APG)

As used herein, "alkyl polyglycoside" or "APG" has a structure as follows, in which "R" is an alkyl or alkenyl group (generally saturated although some may be unsaturated, for example oleoyl, may be present) having 8 to 20 carbons, and "m" is degree of polymerization which is typically 1 to 5:

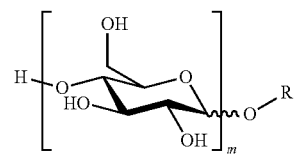

Acyl Glutamate

As used herein, "acyl glutamate" used in compositions of the present invention may have one or more of the following structures, in which R is an alkyl or alkenyl group (generally saturated although some may be unsaturated, for example, oleoyl, may be present) having 8 to 20 carbons and "$M^+$" is cation:

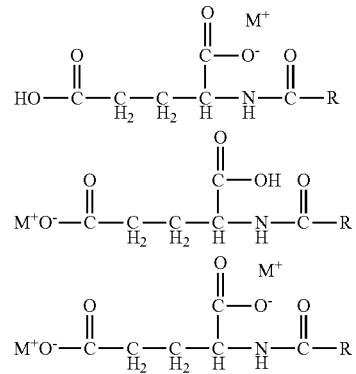

Preferably, the acyl glutamate of the present invention comprises C10-C14 acyl glutamate.

Preferably, the acyl glutamate has one or more cations selected from the group consisting of sodium, potassium, ammonium, substituted ammonium, and any combinations thereof.

Inventors of the present invention discovered surprisingly and unexpectedly that a surfactant system which comprises an APG and an acyl glutamate that are present at specific total levels of the surfactant system, and preferably the APG and the acyl glutamate in specific weight ratios, is not only mild on the skin and/or eyes that are stable especially at acidic pH conditions, but can also deliver benefits such as good sensory rinse-off feel.

A composition of the present invention comprises from 0.5% to 40% by weight of the total composition of a surfactant system which comprises an APG and an acyl glutamate, and wherein the APG and the acyl glutamate are present together at more than 70% of the total surfactant content of the composition ("primary surfactants").

Preferably, the APG and the acyl glutamate are present at more than 80%, preferably more than 90%, more preferably more than 95%, still more preferably more than 98%, by total weight of the surfactant system, wherein preferably the surfactant system consists essentially of the alkyl polyglycoside and the acyl glutamate.

Preferably, the weight ratio of the alkyl polyglycoside to the acyl glutamate is from 0.1 to 9, preferably from 0.4 to 9, more preferably from 1 to 9, still more preferably from 1.5 to 9, alternatively from 1.5 to 2.

The surfactant system or total surfactant level is preferably present in an amount of from 5 wt % to 30 wt %, more preferably from 5 wt % to 20 wt %, and still more preferably from 5 wt % to 15 wt %, alternatively from 7% to 12%, or 8% to 10%, of a rinse-off cleansing composition of the present invention.

A preferred composition comprises a total surfactant level of from 5 wt % to 15 wt %, and has a pH value of from 3.5 to 4.5, preferably from 4 to 4.5, and wherein the weight ratio of the APG to the acyl glutamate is from 1.2 to 9, preferably from 1.5 to 9, and more preferably from 2 to 9.

Another preferred composition comprises a total surfactant level of from 5 wt % to 15 wt %, and has a pH value of greater than 4.5 to 5.5, preferably from 5 to 5.5, and wherein the weight ratio of the APG to the acyl glutamate is greater than 0.1 to 9, preferably from 0.2 to 9, more preferably from 0.4 to 9, still more preferably from 1 to 9, still more preferably from 1.2 to 9, and still more preferably from 1.5 to 9.

Another preferred composition comprises a total surfactant level of from 5 wt % to 15 wt %, and has a pH value of greater than 5.5 to 7.5, preferably greater than 5.5 to 7, more preferably greater than 5.5 to 6.5, and wherein the weight ratio of the APG to the acyl glutamate is from 0.1 to 9, preferably from 0.4 to 9, more preferably from 1 to 9, still more preferably from 1.2 to 9, and still more preferably from 1.5 to 9.

Another preferred composition comprises a total surfactant level greater than 15% to 40%, preferably greater than 15% to 30%, and has a pH value of from 3.5 to 4.5, preferably from 4 to 4.5, and wherein the weight ratio of the APG to the acyl glutamate is from 0.5 to 9, preferably from 1 to 9, more preferably from 1.2 to 9, and still more preferably from 1.5 to 9.

Another preferred composition comprises a total surfactant level greater than 15% to 40%, preferably greater than 15% to 30%, and has a pH value of greater than 4.5 to 5.5, preferably 5 to 5.5, and wherein the weight ratio of the APG to the acyl glutamate is greater than 0.1 to 9, preferably from 0.2 to 9, more preferably from 0.4 to 9, still more preferably from 1 to 9, still more preferably from 1.2 to 9, and still more preferably from 1.5 to 9.

Another preferred composition comprises a total surfactant level greater than 15% to 40%, preferably greater than 15% to 30%, and has a pH value of greater than 5.5 to 7.5, preferably greater than 5.5 to 7, more preferably greater than 5.5 to 6.5, and wherein the weight ratio of the APG to the acyl glutamate is from 0.1 to 9, preferably from 0.2 to 9, more preferably from 0.4 to 9, still more preferably from 1 to 9, still more preferably from 1.2 to 9, and still more preferably from 1.5 to 9.

Advantageously, such surfactant systems are not only mild on the skin and/or eyes but are stable especially at acidic pH conditions and can also deliver benefits such as good sensory rinse-off feel. Such compositions also have simpler formulations having only two surfactants, APG and acyl glutamate. In addition, with fewer ingredients, such compositions are more cost effective.

Advantageously, both APG and acyl glutamate may be naturally derived as the head group of APG and the head group of acyl glutamate may be derived from fermentation of plants, which is desirable as today's consumers are more discerning and appears to prefer products with ingredients that are naturally derived.

Other Surfactants

Other surfactants useful herein include other anionic surfactants (other than the acyl glutamate described hereinabove), other nonionic surfactants (other than the APG described hereinabove), amphoteric surfactants, zwitterionic surfactants, and mixtures thereof. Such surfactants may be detersive surfactants.

A representative, non-limiting, list of suitable other surfactants includes sodium lauryl sarcosinate, sodium lauroyl sarcosinate, lauryl sarcosine, cocoyl sarcosine, sodium tridecyl benzene sulfonate, sodium dodecyl benzene sulfonate, sodium cocoyl isethionate and combinations thereof. The concentration of the anionic surfactant component in the product can be sufficient to provide a desired cleaning and/or lather performance, and generally present in less than 30% of the total level of surfactants in the surfactant system.

Amphoteric detersive surfactants suitable for use in the rinse-off personal care compositions are well known in the art, and include those surfactants broadly described as derivatives of aliphatic secondary and tertiary amines in which an aliphatic radical can be straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate. Other examples of amphoteric surfactants can include sodium lauroamphoacetate, sodium cocoamphoactetate, disodium lauroamphoacetate disodium cocodiamphoacetate, and mixtures thereof. Amphoacetates and diamphoacetates can also be used.

Zwitterionic detersive surfactants suitable for use in the rinse-off personal care compositions are well known in the art, and include those surfactants broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate. Other zwitterionic surfactants can include betaines, including cocoamidopropyl betaine.

Compositions of the present invention may include less than 30%, preferably less than 20%, more preferably less than 10%, still more preferably less than 5%, alternatively less than 3%, or less than 1%, by total weight of the surfactant system, of one or more other surfactants (i.e., beyond alkyl polyglycoside and the acyl glutamate). In one example, the surfactant system is substantially free of or free of other surfactants. The advantage of such a surfactant system is the simplicity of the formula whilst still delivering user-desirable benefits (e.g. stable at acidic pH conditions, good rinse-off feel, mild on skin and/or eyes).

Preferably, such other surfactants, if present, are selected from the group consisting of sarcosinates, glucamides, sulfosuccinates, amphoacetates, sultaines, phosphates, betaines, and any combinations thereof.

Preferably, compositions of the present invention are substantially free of sulfate-based surfactants, and more preferably free of sulfate-based surfactants.

Preferably, compositions of the present invention are substantially free of said other surfactants, and more preferably free of said other surfactants. Advantageously, such compositions are not only mild on the skin and/or eyes, but have simpler formulations having fewer ingredients which is generally desired by some users of the product category. In addition, with fewer ingredients, such compositions are more cost effective.

Solubilizers

A composition of the present invention can also include solubilizers such as sugar alcohols or glycols. Preferably the sugar alcohols can include sorbitol. Preferably the glycols can include propylene glycol, dipropylene glycol, polyethylene glycol, derivatives and combinations thereof. Whilst solubilizers may be included, certain solubilizers, such as polyquaterniums, when present at high levels may cause some degree of ocular irritation. In one example, the compositions of the present invention minimize the amount of solubilizers.

A composition of the present invention may include no more than 10%, preferably no more than 5%, alternatively greater than 0% but less than 3%, or greater than 0% but less than 1%, by total weight of the composition, of a solubilizer.

Preferably, a composition of the present invention is substantially free of solubilizers, and more preferably the composition is free of solubilizers. Advantageously, such compositions are not only mild on the skin and/or eyes, but have simpler formulations with fewer ingredients. In addition, with fewer ingredients, such compositions are more cost effective.

pH Adjusting Agents

A variety of compounds may be used to adjust the pH value of a composition. Such suitable compounds can include, but are not limited to, citric acid, lactic acid, salicylic acid, succinic acid, hydrochloric acid, sodium hydroxide, magnesium hydroxide, triethanol amine, diethanol amine, ethanol amine, monoethanol amine, and any combinations thereof. One preferred example is citric acid as a cost effect approach. The pH adjusting agent may comprise from greater than 0 wt % to 2% of the total weight of the composition.

Optional Ingredients

A variety of optional ingredients can also be added to a personal care composition. Such suitable ingredients can include, but are not limited to, structurants, humectants, fatty acids, inorganic salts, antimicrobial agents or other actives.

Structurants

A composition of the present invention can also include hydrophilic structurants such as carbohydrate structurants and gums. Some suitable carbohydrate structurants include raw starch (corn, rice, potato, wheat, and the like) and pregelatinized starch. Some suitable gums include carrageenan, guar gum and xanthan gum. A personal care composition may include from 0.1% to 30%, from 2% to 25%, or from 4% to 20%, by weight of the personal care composition, of a carbohydrate structurant.

Humectants

A composition of the present invention can also include one or more humectants. Examples of such humectants can include polyhydric alcohols. Further, humectants such as glycerin can be included the personal care composition as a result of production or as an additional ingredient. For example, glycerin can be a by-product after saponification of the personal care composition. Including additional humectant can result in a number of benefits such as improvement in hardness of the personal care composition, decreased water activity of the personal care composition, and reduction of a weight loss rate of the personal care composition over time due to water evaporation. The humectants may comprise from greater than 0 wt % to 10% of the total weight of the composition.

Inorganic Salts

A composition of the present invention can include inorganic salts. Inorganic salts can help to maintain a particular water content or level of the composition and improve hardness of the composition. The inorganic salts can also help to bind the water in the composition to prevent water loss by evaporation or other means. A composition of the present invention can optionally include from 0.01% to 15%, from 1% to 12%, or from 2.5% to 10.5%, by weight of the composition, of inorganic salt. Examples of suitable inorganic salts can include magnesium nitrate, trimagnesium phosphate, calcium chloride, sodium carbonate, sodium aluminum sulfate, disodium phosphate, sodium polymetaphosphate, sodium magnesium succinate, sodium tripolyphosphate, aluminum sulfate, aluminum chloride, aluminum chlorohydrate, aluminum-zirconium trichlorohydrate, aluminum-zirconium trichlorohydrate glycine complex, zinc sulfate, ammonium chloride, ammonium phosphate, calcium acetate, calcium nitrate, calcium phosphate, calcium sulfate, ferric sulfate, magnesium chloride, magnesium sulfate, and tetrasodium pyrophosphate.

Antibacterial Agents

A composition of the present invention can include one or more additional antibacterial agents that can serve to further enhance antimicrobial effectiveness of the personal care composition. A personal care composition can include, for example, from 0.001% to 2%, from 0.01% to 1.5%, or from 0.1% to 1%, by weight of the personal care composition, of additional antibacterial agent(s). Examples of suitable antibacterial agents can include piroctone olamine, carbanilides, triclocarban (also known as trichlorocarbanilide), triclosan, a halogenated diphenylether available as DP-300 from Ciba-Geigy, hexachlorophene, 3,4,5-tribromosalicylanilide, and salts of 2-pyridinethiol-1-oxide, salicylic acid, and other organic acids.

Skin and/or Hair Benefit Agents

A composition of the present invention can include one or more benefit agents or actives. Such personal care compositions can include, for example, from 0.5% to 20%, by weight of the personal care composition, of the benefit agent.

Examples of suitable benefit agents can include petrolatum, glyceryl monooleate, mineral oil, natural oils, and mixtures thereof. Additional examples of benefit agents can include water insoluble or hydrophobic benefit agents.

Non-limiting examples of glycerides suitable for use as hydrophobic skin benefit agents herein can include castor oil, safflower oil, corn oil, walnut oil, peanut oil, olive oil, cod liver oil, almond oil, avocado oil, palm oil, sesame oil, vegetable oils, sunflower seed oil, soybean oil, vegetable oil derivatives, coconut oil and derivatized coconut oil, cottonseed oil and derivatized cottonseed oil, jojoba oil, cocoa butter, and combinations thereof.

Non-limiting examples of alkyl esters suitable for use as hydrophobic skin benefit agents herein can include isopropyl esters of fatty acids and long chain esters of long chain (e.g., C10-C24) fatty acids, e.g., cetyl ricinoleate, non-limiting examples of which can include isopropyl palmitate, isopropyl myristate, cetyl riconoleate, and stearyl riconoleate. Other example can include hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of polyglycerin fatty acid esters suitable for use as hydrophobic skin benefit agents herein can include decaglyceryl distearate, decaglyceryl diisostearate, decaglyceryl monomyriate, decaglyceryl monolaurate, hexaglyceryl monooleate, and combinations thereof.

Preservatives

A composition of the present invention can include one or more preservatives, generally included at less than 2% by total weight of the composition. Such suitable preservatives can include, but are not limited to, benzyl alcohol, kathon, propylene glycol, hydroxy acetophenone, sodium benzoate, disodium ethylenediaminetetraacetic acid (EDTA), parabene, phenoxy ethanol, imidazolidinyl urea, and any combination thereof.

Rinse-Off Personal Care Compositions

Rinse-off personal care compositions of the present invention may come in many forms. For example, a personal care composition may be in a liquid form and could be a body wash, shampoo, conditioning shampoos, body washes, moisturizing body washes, shower gels, skin cleansers, cleansing milks, in shower body moisturizers, pet shampoos, shaving preparations, etc. Rinse-off personal care compositions may also be in a solid form, like in a bar soap or a semi-solid form, like a paste or gel. Solid can also be in many shapes and forms like a rectangle or in a powder or pellet form, for example. Additionally, solid and semi-solid forms may be combined with a substrate to form an article. Rinse-off personal care compositions may also be formulated whereby it can be impregnated into a substrate, for example, open cell foam in the form of dissolvable solid structures. Rinse-off personal care compositions may also be in the form of aerosol foam or foam.

Many personal care compositions can be water-based. It should be understood that an amount of water can be lost, i.e. evaporated, during a process of making a personal care composition, or subsequently, with water being absorbed by surrounding packaging (e.g. a cardboard carton), and the like. Thus, a personal care composition can also include materials that tend to bind the water such that the water can be maintained in the personal care composition at the desired levels. Examples of such materials can include carbohydrate structurants and humectants such as glycerin. In compositions of the present invention, water can be provided in the amount of more than 80%, preferably more than 85%, and more preferably more than 88%, by total weight of the composition. However, it will be appreciated that a personal care composition can be anhydrous.

The personal care composition may be applied by a variety of means, including by rubbing, wiping or dabbing with hands or fingers, or by means of an implement and/or delivery enhancement device. Non-limiting examples of implements include a sponge or sponge-tipped applicator, a mesh shower puff, a swab, a brush, a wipe (e.g., wash cloth), a loofah, and combinations thereof. Non-limiting examples of delivery enhancement devices include mechanical, electrical, ultrasonic and/or other energy devices. Employment of an implement or device may help delivery of the particulate antimicrobial agent to target regions, such as, for example, hair follicles and undulations that can exist in the underarm. The rinse-off care product may be sold together with such an implement or device. Alternatively, an implement or device can be sold separately but contain indicium to indicate usage with a rinse-off care product. Implements and delivery devices can employ replaceable portions (e.g., the skin interaction portions), which can be sold separately or sold together with the rinse-off care product in a kit.

TESTS

Test for Measuring Stability

Stability of a sample is measured by determining whether there is appearance of a precipitate in the sample after a predetermined period under a predetermined condition. Appearance of a precipitate is determined by naked eye observation.

During the test, the laboratory temperature is controlled at 23° C.+/−2° C. (room temperature). 20 ml of a sample is added in a 20 ml glass bottle (Vial 03-339-21K Fisherbrand™ Class B available from Fisher scientific). The sample in the glass bottle is observed by the naked eye for the appearance of a precipitate. If no precipitate is observed, the sample is considered stable under room temperature; if a precipitate is observed, the sample is considered unstable under room temperature.

The glass bottle containing the sample is then stored in a temperature controlled chamber under one of the following conditions: (i) −18° C. for 2 days; or (ii) 5° C. for 1 week. The glass bottle is then taken out of the chamber after the respective predetermined period and condition and kept at room temperature for one day. On the second day, the sample is observed by the naked eye for the appearance of a precipitate. If no precipitate is observed, the sample is considered stable after the predetermined period under the predetermined condition; if a precipitate is observed, the sample is considered unstable after the predetermined period under the predetermined condition.

Test for Measuring Rinse-Off Property

Rinse-off property of a sample is measured by a qualitative method in which trained beauty panelists evaluate sensory rinse-off feel of a sample based on a Scale of 1 to 5, in which:

1: represents coated feel
    2: represents residue feel
    3: represents low residue feel
    4: represents no residue feel
    5: represents squeaky feel A water tap (Broen) is set to provide running water at the following conditions: (i) water flow-rate of 50 ml/s; (ii) water temperature at 27° C.+/−2° C.; and (iii) water hardness of 3 gpg. The panelists are asked to perform the following instructions and subsequently rate the sample based on the Scale described above.

In a first step, pre-wash hands with a clarifying soap (Safeguard® White Soap) and dry hands with a cotton towel to create a baseline. In a second step, evenly coat the palms and the back of hands with 50 µl of Artificial Sebum (Artificial Sebum provided by Advanced Testing Laboratory). In a third step, wet hands with running water from the water tap (1 second back and forth) and 1 gram of the sample is dosed on one palm. In a fourth step, rub both palms together to complete 5 complete circular rotations. In a fifth step, using the palm of one hand, rub across the back of the other hand to complete one circular rotation. Repeat for the other hand to complete 1 cycle. Repeat this cycle 5 times. In a sixth step, rub both palms together with 5 complete circular rotations (like in the fourth step above). In a seventh step, remove lather generated into a weighing boat to record its weight. In an eighth step, rinse hands under running water from the water tap for 5 seconds to remove lather from the hands. In a ninth step, use any finger on the right hand to rub the palm of the left hand in a single stroke to assess ease of friction to determine the sensory rinse-off feel of the sample based on the Scale described above. Each sample is evaluated by three different panelists and an average rating is taken. Generally, a rating of 3 or higher on the Scale described above is desirable for a sample to be regarded as having good rinse-off property.

Test for Measuring Foam Creaminess and Foam Stability

Foam quality of a sample may be measured by means of the foam creaminess and/or the foam stability of a sample. Foam creaminess and foam stability of a sample is measured by a foam analyzer instrument (such as Kruss DFA 100 Foam Analyzer, or equivalent). Materials that are required for the instrument set up includes (i) Kruss DFA 100 Foam Analyzer; (ii) SH4512—Column holder with FI4511 seal; (iii) SR4501—Two-bladed stirring head with anti-adhesion coating; (iv) CY4572—Prism column (40 mm) with calibration grid for foam structure analyses; (v) L4770 Avery sticker label (45.7×25.4 mm); (vi) Measuring cups; (vii) 25 ml and 5 ml syringes; (viii) Paper towels; and (ix) Water—Deionized water.

The instrument setup is described in the following steps: (i) Set camera height to 5.5 cm (camera is part of the Kruss DFA 100 Foam Analyzer); (ii) Set height illumination–$\lambda$=469 nm; (iii) Set camera distance at 'position 2'; (iv) Adjust camera focus to 1.4; (v) Insert the SR4501 stirring head onto the SH4512 column holder; (vi) Place the FI4511 seal into the groove of the SH4512 column holder and place the CY4572 prism column on top of the FI4511 seal; (vii) Attach the L4770 Avery sticker label at top side of the CY4572 prism column (i e the side that is opposite from the side that is placed on top of the FI4511 seal; (viii) Insert the assembled SH4512 column holder into the Kruss DFA 100 Foam Analyzer; (ix) Ensure the CY4572 prism column is accurately aligned straight towards the instrument; and (x) View 'Live camera' from analysis software (analysis software comes together with the Kruss DFA 100 Foam Analyzer) to ensure camera is capturing unobstructed full view of the CY4572 prism column surface.

Each sample is prepared as follows. In a first step, using syringes, 5 ml of a sample and 45 ml of deionized water are added into a measuring cup to make up a final volume of 50 ml (which is the minimum amount required for analysis with the instrument). In a second step, the content in the measuring cup is gently mixed (do not create bubbles) until it becomes a homogenous solution. In a third step, using a syringe, gently add the homogenous solution into the CY4572 prism column to minimize bubble generation.

The analysis software program setup is described in the following steps: (i) Set stirring speed at 3,000 rpm; (ii) Set oscillation period at 2 seconds; (iii) Set stirrer rotation cycle to 30 seconds with a pause for 10 seconds, and repeat the rotation cycle 3 times; (iv) After the third rotation cycle is completed, mean bubble area of the foam generated is first measured at 120 seconds (mean bubble area @ 120 seconds) and then at 230 seconds (mean bubble area @ 230 seconds) immediately after the third rotation cycle is completed.

Based on the method as described above, foam creaminess is determined by measuring the mean bubble area @ 120 seconds. Generally, the lower the value of the mean bubble area @ 120 seconds (foam creaminess value), the better the foam creaminess.

Based on the method as described above, foam stability is determined by measuring the mean bubble area @ 120 seconds and measuring the mean bubble area @ 230 seconds, followed by applying the following computation to obtain a foam stability value:

Foam Stability Value=Mean bubble area @ 230 seconds–Mean bubble area @ 120 seconds/110

Generally, the lower the foam stability value, the better the foam stability.

EXAMPLES

Test Sample Preparation

Exemplary rinse-off cleansing compositions for the present invention are provided as follows in Tables 1A to 1D below:

TABLE 1A

| Ingredients (wt %) | Ex. 1 | Ex. 2 | Ex. 3 | Ex. 4 | Ex. 5 | Ex. 6 | Ex. 7 | Ex. 8 |
| --- | --- | --- | --- | --- | --- | --- | --- | --- |
| Decyl Glucoside (A) | 2.5% | 3.5% | 4.5% | 6.0% | 10.0% | 14.0% | 18.0% | 10.0% |
| Sodium Cocoyl Glutamate (B) | 2.5% | 1.5% | 0.5% | 14.0% | 10.0% | 6.0% | 2.0% | 10.0% |
| Total Surfactant (A + B) | 5.0% | 5.0% | 5.0% | 20.0% | 20.0% | 20.0% | 20.0% | 20.0% |
| Weight Ratio of A:B | 1.00 | 2.33 | 9.00 | 0.43 | 1.00 | 2.33 | 9.00 | 1.00 |
| Citric Acid | Balance pH to 4.0 | Balance pH to 4.0 | Balance pH to 4.0 | Balance pH to 4.0 | Balance pH to 4.0 | Balance pH to 4.0 | Balance pH to 4.0 | Balance pH to 4.4 |
| Water | Q.S. | Q.S. | Q.S. | Q.S. | Q.S. | Q.S. | Q.S. | Q.S. |

TABLE 1B

| Ingredients (wt %) | Ex. 9 | Ex. 10 | Ex. 11 | Ex. 12 | Ex. 13 | Ex. 14 |
| --- | --- | --- | --- | --- | --- | --- |
| Decyl Glucoside (A) | 0.5% | 1.5% | 2.5% | 6.0% | 10.0% | 14.0% |
| Sodium Cocoyl Glutamate (B) | 4.5% | 3.5% | 2.5% | 14.0% | 10.0% | 6.0% |
| Total Surfactant (A + B) | 5.0% | 5.0% | 5.0% | 20.0% | 20.0% | 20.0% |
| Weight Ratio of A:B | 0.11 | 0.43 | 1.00 | 0.43 | 1.00 | 2.33 |
| Citric Acid | Balance pH to 5.0 | Balance pH to 5.0 | Balance pH to 5.0 | Balance pH to 5.0 | Balance pH to 5.0 | Balance pH to 5.0 |
| Water | Q.S. | Q.S. | Q.S. | Q.S. | Q.S. | Q.S. |

TABLE 1C

| Ingredients (wt %) | Ex. 15 | Ex. 16 | Ex. 17 | Ex. 18 | Ex. 19 | Ex. 20 | Ex. 21 | Ex. 22 | Ex. 23 | Ex. 24 | Ex. 25 |
|---|---|---|---|---|---|---|---|---|---|---|---|
| Decyl Glucoside (A) | 0.5% | 1.5% | 2.5% | 3.5% | 4.5% | 5.0% | 2.0% | 6.0% | 10.0% | 14.0% | 18.0% |
| Sodium Cocoyl Glutamate (B) | 4.5% | 3.5% | 2.5% | 1.5% | 0.5% | 5.0% | 18.0% | 14.0% | 10.0% | 6.0% | 2.0% |
| Total Surfactant (A + B) | 5.0% | 5.0% | 5.0% | 5.0% | 5.0% | 10.0% | 20.0% | 20.0% | 20.0% | 20.0% | 20.0% |
| Weight Ratio of A:B | 0.11 | 0.43 | 1.00 | 2.33 | 9.00 | 1.00 | 0.11 | 0.43 | 1.00 | 2.33 | 9.00 |
| Citric Acid | Balance pH to 5.5 | Balance pH to 5.5 | Balance pH to 5.5 | Balance pH to 5.5 | Balance pH to 5.5 | Balance pH to 5.5 | Balance pH to 5.5 | Balance pH to 5.5 | Balance pH to 5.5 | Balance pH to 5.5 | Balance pH to 5.5 |
| Water | Q.S. | Q.S. | Q.S. | Q.S. | Q.S. | Q.S. | Q.S. | Q.S. | Q.S. | Q.S. | Q.S. |

TABLE 1D

| Ingredients (wt %) | Ex. 26 | Ex. 27 | Ex. 28 | Ex. 29 | Ex. 30 | Ex. 31 | Ex. 32 | Ex. 33 | Ex. 34 | Ex. 35 | Ex. 36 |
|---|---|---|---|---|---|---|---|---|---|---|---|
| Decyl Glucoside (A) | 0.5% | 1.5% | 2.5% | 3.5% | 4.5% | 14.0% | 2.0% | 6.0% | 10.0% | 14.0% | 18.0% |
| Sodium Cocoyl Glutamate (B) | 4.5% | 3.5% | 2.5% | 1.5% | 0.5% | 6.0% | 18.0% | 14.0% | 10.0% | 6.0% | 2.0% |
| Total Surfactant (A + B) | 5.0% | 5.0% | 5.0% | 5.0% | 5.0% | 20.0% | 20.0% | 20.0% | 20.0% | 20.0% | 20.0% |
| Weight Ratio of A:B | 0.11 | 0.43 | 1.00 | 2.33 | 9.00 | 2.33 | 0.11 | 0.43 | 1.00 | 2.33 | 9.00 |
| Citric Acid | Balance pH to 7.0 | Balance pH to 7.0 | Balance pH to 7.0 | Balance pH to 7.0 | Balance pH to 7.0 | Balance pH to 6.0 | Balance pH to 7.0 | Balance pH to 7.0 | Balance pH to 7.0 | Balance pH to 7.0 | Balance pH to 7.0 |
| Water | Q.S. | Q.S. | Q.S. | Q.S. | Q.S. | Q.S. | Q.S. | Q.S. | Q.S. | Q.S. | Q.S. |

Each of the above-described rinse-off cleansing compositions (test samples) is prepared as follows. A mixing blade (e.g. mixing equipment IKA Eurostar 200 Digital with blade: 1-7125-33 (80 mm, pitched-blade turbine) and a beaker is cleaned and sanitized with 70% alcohol. Two surfactants, sodium cocoylglutamate (Amisoft® ECS-22W) and decyl glucoside (Plantacare® 2000UP) are added into the beaker. A mixing blade is then inserted into the beaker and the ingredients in the beaker is mixed for about 15 minutes at a mixing speed of 200 rpm until all ingredients are visually well dispersed. 80% of deionized water (DI water) is then added to the solution while mixing, and the mixing continues for about 10 minutes at a mixing speed of 200 rpm until all ingredients are visually well dispersed. Citric acid is then added to the solution while mixing, and the mixing continues for about 10 minutes at a mixing speed of 200 rpm until all ingredients are visually well dispersed. 95 wt % of deionized water is then added to the solution while mixing, and the mixing continues for about 5 minutes at a mixing speed of 200 rpm until all ingredients are visually well dispersed. pH of the solution is adjusted to the desired pH with citric acid and deionized water is added, where required, to Q.S. The solution is then mixed for about 10 minutes at a mixing speed of 200 rpm until all ingredients are visually well dispersed and the final pH of the solution is checked.

Comparative Test to Show Impact of Different APG/Acyl Glutamate Ratios at Different pH Values on Composition Stability The stability of each of the test samples is measured using the test method for measuring stability as described above, and the results are shown in Tables 2 to 5 hereinafter. Symbol "I"=Precipitate observed; and Symbol "X"=No precipitate observed.

TABLE 2

| Ingredients (wt %)/ Predetermined Conditions | Ex. 1 | Ex. 2 | Ex. 3 | Ex. 4 | Ex. 5 | Ex. 6 | Ex. 7 | Ex. 8 |
|---|---|---|---|---|---|---|---|---|
| Decyl Glucoside (A) | 2.5% | 3.5% | 4.5% | 6.0% | 10.0% | 14.0% | 18.0% | 10.0% |
| Sodium Cocoyl Glutamate (B) | 2.5% | 1.5% | 0.5% | 14.0% | 10.0% | 6.0% | 2.0% | 10.0% |
| Total Surfactant (A + B) | 5.0% | 5.0% | 5.0% | 20.0% | 20.0% | 20.0% | 20.0% | 20.0% |
| Weight Ratio of A:B | 1.00 | 2.33 | 9.00 | 0.43 | 1.00 | 2.33 | 9.00 | 1.00 |

TABLE 2-continued

| Ingredients (wt %)/ Predetermined Conditions | Ex. 1 | Ex. 2 | Ex. 3 | Ex. 4 | Ex. 5 | Ex. 6 | Ex. 7 | Ex. 8 |
|---|---|---|---|---|---|---|---|---|
| Initial observation at room temperature 23° C. +/− 2° C. (RT) | \| | X | X | X | X | X | X | X |
| −18° C. for 2 days, then RT for 1 day | \| | X | X | X | X | X | X | X |
| 5° C. for 1 week, then RT for 1 day | \| | X | X | \| | X | X | X | X |
| pH value | 4.0 | 4.0 | 4.0 | 4.0 | 4.0 | 4.0 | 4.0 | 4.4 |

A stable composition is characterized herein by: (i) no precipitate observed at the initial observation at room temperature; (ii) no precipitate observed when the composition is subjected to a predetermined condition of −18° C. for 2 days, then RT for 1 day; or (iii) no precipitate observed when the composition is subjected to a predetermined condition of 5° C. for 1 week, then RT for 1 day; preferably no precipitate observed under the predetermined conditions in (i) and (ii) above; and more preferably no precipitate observed under the predetermined conditions in (i), (ii) and (iii) above.

Based on the table above, for compositions that comprise 5 wt % of the surfactant system at pH value of 4.0, preferred compositions are those with a weight ratio of the APG to the acyl glutamate that is greater than 1 (Examples 2 and 3). For compositions that comprise 20 wt % of the surfactant system at pH value of 4.0 or 4.4, preferred compositions are those with a weight ratio of the APG to the acyl glutamate that is greater than 0.4 (Examples 4 to 8), and more preferred compositions are those with a weight ratio of the APG to the acyl glutamate from 1 (Examples 5 to 8).

TABLE 3

| Ingredients (wt %)/ Predetermined Conditions | Ex. 9 | Ex. 10 | Ex. 11 | Ex. 12 | Ex. 13 | Ex. 14 |
|---|---|---|---|---|---|---|
| Decyl Glucoside (A) | 0.5% | 1.5% | 2.5% | 6.0% | 10.0% | 14.0% |
| Sodium Cocoyl Glutamate (B) | 4.5% | 3.5% | 2.5% | 14.0% | 10.0% | 6.0% |
| Total Surfactant (A + B) | 5.0% | 5.0% | 5.0% | 20.0% | 20.0% | 20.0% |
| Weight Ratio of A:B | 0.11 | 0.43 | 1.00 | 0.43 | 1.00 | 2.33 |
| Initial observation at room temperature 23° C. +/− 2° C. (RT) | X | X | X | X | X | X |
| −18° C. for 2 days, then RT for 1 day | \| | X | X | X | X | X |
| 5° C. for 1 week, then RT for 1 day | \| | X | X | X | X | X |
| pH value | 5.0 | 5.0 | 5.0 | 5.0 | 5.0 | 5.0 |

Based on the table above, for compositions that comprise 5 wt % of the surfactant system at pH value of 5.0, preferred compositions are those with a weight ratio of the APG to the acyl glutamate that is greater than 0.1, and preferably greater than 0.4 (Examples 10 and 11). For compositions that comprise 20 wt % of the surfactant system at pH value of 5.0, preferred compositions are those with a weight ratio of the APG to the acyl glutamate that is greater than 0.1, and preferably greater than 0.4 (Examples 12 to 14).

TABLE 4

| Ingredients (wt %)/ Predetermined Conditions | Ex. 15 | Ex. 16 | Ex. 17 | Ex. 18 | Ex. 19 | Ex. 20 | Ex. 21 | Ex. 22 | Ex. 23 | Ex. 24 | Ex. 25 |
|---|---|---|---|---|---|---|---|---|---|---|---|
| Decyl Glucoside (A) | 0.5% | 1.5% | 2.5% | 3.5% | 4.5% | 5.0% | 2.0% | 6.0% | 10.0% | 14.0% | 18.0% |
| Sodium Cocoyl Glutamate (B) | 4.5% | 3.5% | 2.5% | 1.5% | 0.5% | 5.0% | 18.0% | 14.0% | 10.0% | 6.0% | 2.0% |
| Total Surfactant (A + B) | 5.0% | 5.0% | 5.0% | 5.0% | 5.0% | 10.0% | 20.0% | 20.0% | 20.0% | 20.0% | 20.0% |
| Weight Ratio of A:B | 0.11 | 0.43 | 1.00 | 2.33 | 9.00 | 1.00 | 0.11 | 0.43 | 1.00 | 2.33 | 9.00 |
| Initial observation at room temperature 23° C. +/− 2° C. (RT) | X | X | X | X | X | X | X | X | X | X | X |
| −18° C. for 2 days, then RT for 1 day | | X | X | X | X | X | | X | X | X | X |
| 5° C. for 1 week, then RT for 1 day | | X | X | X | X | X | | X | X | X | X |
| pH value | 5.5 | 5.5 | 5.5 | 5.5 | 5.5 | 5.5 | 5.5 | 5.5 | 5.5 | 5.5 | 5.5 |

Based on the table above, for compositions that comprise 5 wt % of the surfactant system at pH value of 5.5, preferred compositions are those with a weight ratio of the APG to the acyl glutamate that is greater than 0.1, and preferably greater than 0.4 (Examples 16 to 19). For compositions that comprise 20 wt % of the surfactant system at pH value of 5.5, preferred compositions are those with a weight ratio of the APG to the acyl glutamate that is greater than 0.1, and preferably greater than 0.4 (Examples 22 to 25). The composition that comprises 10 wt % of the surfactant system at pH value of 5.5 with a weight ratio of the APG to the acyl glutamate that is 1, is also a preferred composition (Example 20).

TABLE 5

| Ingredients (wt %)/ Predetermined Conditions | Ex. 26 | Ex. 27 | Ex. 28 | Ex. 29 | Ex. 30 | Ex. 31 | Ex. 32 | Ex. 33 | Ex. 34 | Ex. 35 | Ex. 36 |
|---|---|---|---|---|---|---|---|---|---|---|---|
| Decyl Glucoside (A) | 0.5% | 1.5% | 2.5% | 3.5% | 4.5% | 14.0% | 2.0% | 6.0% | 10.0% | 14.0% | 18.0% |
| Sodium Cocoyl Glutamate (B) | 4.5% | 3.5% | 2.5% | 1.5% | 0.5% | 6.0% | 18.0% | 14.0% | 10.0% | 6.0% | 2.0% |
| Total Surfactant (A + B) | 5.0% | 5.0% | 5.0% | 5.0% | 5.0% | 20.0% | 20.0% | 20.0% | 20.0% | 20.0% | 20.0% |
| Weight Ratio of A:B | 0.11 | 0.43 | 1.00 | 2.33 | 9.00 | 2.33 | 0.11 | 0.43 | 1.00 | 2.33 | 9.00 |
| Initial observation at room temperature 23° C. +/− 2° C. (RT) | X | X | X | X | X | X | X | X | X | X | X |
| −18° C. for 2 days, then RT for 1 day | X | X | X | X | X | X | X | X | X | X | X |
| 5° C. for 1 week, then RT for 1 day | X | X | X | X | X | X | X | X | X | X | X |
| pH value | 7.0 | 7.0 | 7.0 | 7.0 | 7.0 | 6.0 | 7.0 | 7.0 | 7.0 | 7.0 | 7.0 |

Based on the table above, preferred compositions are all the compositions (5 wt % to 20 wt % of the surfactant system) which have a pH value of 6.0 or 7.0 and with a weight ratio of the APG to the acyl glutamate from 0.1 (Examples 26 to 36). Although it may be possible for compositions to have with a weight ratio of the APG to the acyl glutamate to be less than 0.1, it may be less cost effective to go below the 0.1 weight ratio.

Comparative Test to Show Impact of Total Surfactant System Level at Different pH Values on Composition Rinse-Off Property The rinse-off property of each of the test samples is measured using the test method for measuring rinse-off property as described above, and the results are shown in Tables 6 to 9 hereinafter. The trained panelists evaluate sensory rinse-off feel of a sample based on a Scale of 1 to 5, in which:
- 1: represents coated feel
- 2: represents residue feel
- 3: represents low residue feel
- 4: represents no residue feel
- 5: represents squeaky feel Generally, a rating of 3 or higher on the Scale of 1 to 5 as described above is desirable for a sample to be regarded as having good rinse-off property.

TABLE 6

| Ingredients (wt %)/ Sensory Rinse-off Feel | Ex. 1 | Ex. 2 | Ex. 3 | Ex. 4 | Ex. 5 | Ex. 6 | Ex. 7 | Ex. 8 |
|---|---|---|---|---|---|---|---|---|
| Decyl Glucoside (A) | 2.5% | 3.5% | 4.5% | 6.0% | 10.0% | 14.0% | 18.0% | 10.0% |
| Sodium Cocoyl Glutamate (B) | 2.5% | 1.5% | 0.5% | 14.0% | 10.0% | 6.0% | 2.0% | 10.0% |
| Total Surfactant (A + B) | 5.0% | 5.0% | 5.0% | 20.0% | 20.0% | 20.0% | 20.0% | 20.0% |
| Weight Ratio of A:B | 1.00 | 2.33 | 9.00 | 0.43 | 1.00 | 2.33 | 9.00 | 1.00 |
| pH value | 4.0 | 4.0 | 4.0 | 4.0 | 4.0 | 4.0 | 4.0 | 4.4 |
| On a Scale of 1 to 5 | 4 | 4 | 4 | 3 | 3 | 3 | 3 | 3 |

Based on the table above, for compositions that comprise 5 wt % of the surfactant system at pH value of 4.0 and with a weight ratio of the APG to the acyl glutamate from 1, all of these compositions have a rating of 4 and are thus regarded as having good rinse-off property (Examples 1 to 3). For compositions that comprise 20 wt % of the surfactant system at pH value of 4.0 or 4.4 and with a weight ratio of the APG to the acyl glutamate greater than 0.4, all of these compositions have a rating of 3 and are thus regarded as having good rinse-off property (Examples 4 to 8).

TABLE 7

| Ingredients (wt %)/ Sensory Rinse-off Feel | Ex. 9 | Ex. 10 | Ex. 11 | Ex. 12 | Ex. 13 | Ex. 14 |
|---|---|---|---|---|---|---|
| Decyl Glucoside (A) | 0.5% | 1.5% | 2.5% | 6.0% | 10.0% | 14.0% |
| Sodium Cocoyl Glutamate (B) | 4.5% | 3.5% | 2.5% | 14.0% | 10.0% | 6.0% |
| Total Surfactant (A + B) | 5.0% | 5.0% | 5.0% | 20.0% | 20.0% | 20.0% |
| Weight Ratio of A:B | 0.11 | 0.43 | 1.00 | 0.43 | 1.00 | 2.33 |
| pH value | 5.0 | 5.0 | 5.0 | 5.0 | 5.0 | 5.0 |
| On a Scale of 1 to 5 | 4 | 4 | 4 | 3 | 3 | 3 |

Based on the table above, for compositions that comprise 5 wt % of the surfactant system at pH value of 5.0 and with a weight ratio of the APG to the acyl glutamate from 0.1, all of these compositions have a rating of 4 and are thus regarded as having good rinse-off property (Examples 9 to 11). For compositions that comprise 20 wt % of the surfactant system at pH value of 5.0 and with a weight ratio of the APG to the acyl glutamate greater than 0.1, all of these compositions have a rating of 3 and are thus regarded as having good rinse-off property (Examples 12 to 14).

TABLE 8

| Ingredients (wt %)/ Sensory Rinse-off Feel | Ex. 15 | Ex. 16 | Ex. 17 | Ex. 18 | Ex. 19 | Ex. 20 | Ex. 21 | Ex. 22 | Ex. 23 | Ex. 24 | Ex. 25 |
|---|---|---|---|---|---|---|---|---|---|---|---|
| Decyl Glucoside (A) | 0.5% | 1.5% | 2.5% | 3.5% | 4.5% | 5.0% | 2.0% | 6.0% | 10.0% | 14.0% | 18.0% |
| Sodium Cocoyl Glutamate (B) | 4.5% | 3.5% | 2.5% | 1.5% | 0.5% | 5.0% | 18.0% | 14.0% | 10.0% | 6.0% | 2.0% |
| Total Surfactant (A + B) | 5.0% | 5.0% | 5.0% | 5.0% | 5.0% | 10.0% | 20.0% | 20.0% | 20.0% | 20.0% | 20.0% |
| Weight Ratio of A:B | 0.11 | 0.43 | 1.00 | 2.33 | 9.00 | 1.00 | 0.11 | 0.43 | 1.00 | 2.33 | 9.00 |
| pH value | 5.5 | 5.5 | 5.5 | 5.5 | 5.5 | 5.5 | 5.5 | 5.5 | 5.5 | 5.5 | 5.5 |
| On a Scale of 1 to 5 | 4 | 4 | 4 | 4 | 4 | 3 | 3 | 3 | 3 | 3 | 3 |

Based on the table above, for compositions that comprise 5 wt % of the surfactant system at pH value of 5.5 and with a weight ratio of the APG to the acyl glutamate from 0.1, all of these compositions have a rating of 4 and are thus regarded as having good rinse-off property (Examples 15 to 19). For compositions that comprise 20 wt % of the surfactant system at pH value of 5.5 and with a weight ratio of the APG to the acyl glutamate from 0.1, all of these compositions have a rating of 3 and are thus regarded as having good rinse-off property (Examples 21 to 25). The composition that comprises 10 wt % of the surfactant system at pH value of 5.5 with a weight ratio of the APG to the acyl glutamate that is 1, also has a rating of 3 and is thus regarded as having good rinse-off property (Example 20).

TABLE 9

| Ingredients (wt %)/ Sensory Rinse-off Feel | Ex. 26 | Ex. 27 | Ex. 28 | Ex. 29 | Ex. 30 | Ex. 31 | Ex. 32 | Ex. 33 | Ex. 34 | Ex. 35 | Ex. 36 |
|---|---|---|---|---|---|---|---|---|---|---|---|
| Decyl Glucoside (A) | 0.5% | 1.5% | 2.5% | 3.5% | 4.5% | 14.0% | 2.0% | 6.0% | 10.0% | 14.0% | 18.0% |
| Sodium Cocoyl Glutamate (B) | 4.5% | 3.5% | 2.5% | 1.5% | 0.5% | 6.0% | 18.0% | 14.0% | 10.0% | 6.0% | 2.0% |
| Total Surfactant (A + B) | 5.0% | 5.0% | 5.0% | 5.0% | 5.0% | 20.0% | 20.0% | 20.0% | 20.0% | 20.0% | 20.0% |
| Weight Ratio of A:B | 0.11 | 0.43 | 1.00 | 2.33 | 9.00 | 2.33 | 0.11 | 0.43 | 1.00 | 2.33 | 9.00 |
| pH value | 7.0 | 7.0 | 7.0 | 7.0 | 7.0 | 6.0 | 7.0 | 7.0 | 7.0 | 7.0 | 7.0 |
| On a Scale of 1 to 5 | 4 | 4 | 4 | 4 | 4 | 3 | 3 | 3 | 3 | 3 | 3 |

Based on the table above, for compositions that comprise 5 wt % of the surfactant system at pH value of 7.0 and with a weight ratio of the APG to the acyl glutamate from 0.1, all of these compositions have a rating of 4 and are thus regarded as having good rinse-off property (Examples 26 to 30). For compositions that comprise 20 wt % of the surfactant system at pH value of 6.0 or 7.0 and with a weight ratio of the APG to the acyl glutamate from 0.1, all of these compositions have a rating of 3 and are thus regarded as having good rinse-off property (Examples 31 to 36).

In summary, based on Tables 6 to 9 above, all the compositions (Examples 1 to 36) have a rating of either 3 or 4 and are regarded to have good rinse-off property. It is surprising to note that compositions that comprise a lower total surfactant system level have a higher rating of 4 as compared to compositions that comprise a higher total surfactant system level (rating of 3). It is also surprising to note that pH value does not appear to affect the rinse-off property of the compositions. Even though some of the compositions may be less desirable in terms of composition stability under certain predetermined conditions (such as Examples 1, 9, 15, 21), all of the compositions are regarded to have good rinse-off property and can deliver a good sensory rinse-off benefit which is desired by consumers.

Comparative Test to Show Impact of Different APG/Acyl Glutamate Ratios at Different pH Values on Composition Foam Creaminess and Composition Foam Stability The foam creaminess and foam stability of each of the test samples is measured using the test method for measuring foam creaminess and foam stability as described above, and the results are shown in Tables 10 to 13 hereinafter.

Generally, the lower the value of the mean bubble area @ 120 seconds (foam creaminess value), the better the foam creaminess. In one example, for a sample to be regarded as having good foam creaminess, it is acceptable to have a foam creaminess value of less than 2000, and preferably less than 1500.

Generally, the lower the foam stability value (Foam Stability Value=Mean bubble area @ 230 seconds—Mean bubble area @ 120 seconds/110), the better the foam stability. In one example, a foam stability value of less than 11 is acceptable, preferably less than 7, and more preferably less than 5.

TABLE 10

| Ingredients (wt %)/ Value of Foam Creaminess and Foam Stability | Ex. 2 | Ex. 3 | Ex. 4 | Ex. 5 | Ex. 6 | Ex. 7 | Ex. 8 |
|---|---|---|---|---|---|---|---|
| BDecyl Glucoside (A) | 3.5% | 4.5% | 6.0% | 10.0% | 14.0% | 18.0% | 10.0% |
| Sodium Cocoyl Glutamate (B) | 1.5% | 0.5% | 14.0% | 10.0% | 6.0% | 2.0% | 10.0% |
| Total Surfactant (A + B) | 5.0% | 5.0% | 20.0% | 20.0% | 20.0% | 20.0% | 20.0% |
| Weight Ratio of A:B | 2.33 | 9.00 | 0.43 | 1.00 | 2.33 | 9.00 | 1.00 |
| pH value | 4.0 | 4.0 | 4.0 | 4.0 | 4.0 | 4.0 | 4.4 |
| Foam Creaminess Value | 1489 | 1772 | 1404 | 1384 | 1407 | 1576 | 1384 |
| Foam Stability Value | 4.29 | 9.60 | −2.50 | −0.30 | 0.18 | 4.55 | −0.30 |

Based on the table above, for compositions that comprise 5 wt % of the surfactant system at pH value of 4.0 and with a weight ratio of the APG to the acyl glutamate greater than 1, all of these compositions have foam creaminess values and foam stability values that are acceptable (Examples 2 and 3). Preferred compositions in terms of foam creaminess and foam stability is Example 2, in which the foam creaminess value is less than 1500 and the foam stability value is less than 5.

For compositions that comprise 20 wt % of the surfactant system at pH value of 4.0 or 4.4 and with a weight ratio of the APG to the acyl glutamate greater than 0.4, all of these compositions also have foam creaminess values and foam stability values that are acceptable (Examples 4 to 8). Preferred compositions in terms of foam creaminess are Examples 4, 5, 6 and 8, in which the foam creaminess value is less than 1500. Preferred compositions in terms of foam stability are Examples 4 to 8, in which the foam stability value is less than 5.

TABLE 11

| Ingredients (wt %)/ Value of Foam Creaminess and Foam Stability | Ex. 9 | Ex. 10 | Ex. 11 | Ex. 13 | Ex. 14 |
|---|---|---|---|---|---|
| Decyl Glucoside (A) | 0.5% | 1.5% | 2.5% | 10.0% | 14.0% |
| Sodium Cocoyl Glutamate (B) | 4.5% | 3.5% | 2.5% | 10.0% | 6.0% |
| Total Surfactant (A + B) | 5.0% | 5.0% | 5.0% | 20.0% | 20.0% |
| Weight Ratio of A:B | 0.11 | 0.43 | 1.00 | 1.00 | 2.33 |
| pH value | 5.0 | 5.0 | 5.0 | 5.0 | 5.0 |
| Foam Creaminess Value | 1635 | 1389 | 1463 | 1639 | 1574 |
| Foam Stability Value | 5.05 | −0.24 | 5.76 | 3.23 | 0.14 |

Based on the table above, for compositions that comprise 5 wt % of the surfactant system at pH value of 5.0 and with a weight ratio of the APG to the acyl glutamate from 0.1, all of these compositions have foam creaminess values and foam stability values that are acceptable (Examples 9 to 11). Preferred compositions in terms of foam creaminess are Examples 10 and 11, in which the foam creaminess value is less than 1500. Preferred compositions in terms of foam stability is Example 12, in which the foam stability value is less than 5.

For compositions that comprise 20 wt % of the surfactant system at pH value of 5.0 and with a weight ratio of the APG to the acyl glutamate greater than 0.4, all of these compositions also have foam creaminess values and foam stability values that are acceptable (Examples 13 and 14). Preferred compositions in terms of foam stability are Examples 13 and 14, in which the foam stability value is less than 5.

TABLE 12

| Ingredients (wt %)/Value of Foam Creaminess and Foam Stability | Ex. 16 | Ex. 17 | Ex. 18 | Ex. 19 | Ex. 20 | Ex. 22 | Ex. 23 | Ex. 24 | Ex. 25 |
|---|---|---|---|---|---|---|---|---|---|
| Decyl Glucoside (A) | 1.5% | 2.5% | 3.5% | 4.5% | 5.0% | 6.0% | 10.0% | 14.0% | 18.0% |
| Sodium Cocoyl Glutamate (B) | 3.5% | 2.5% | 1.5% | 0.5% | 5.0% | 14.0% | 10.0% | 6.0% | 2.0% |
| Total Surfactant (A + B) | 5.0% | 5.0% | 5.0% | 5.0% | 10.0% | 20.0% | 20.0% | 20.0% | 20.0% |
| Weight Ratio of A:B | 0.43 | 1.00 | 2.33 | 9.00 | 1.00 | 0.43 | 1.00 | 2.33 | 9.00 |
| pH value | 5.5 | 5.5 | 5.5 | 5.5 | 5.5 | 5.5 | 5.5 | 5.5 | 5.5 |
| Foam Creaminess Value | 1389 | 1741 | 1795 | 1837 | 1463 | 1573 | 1571 | 1663 | 1850 |
| Foam Stability Value | −0.24 | 6.63 | 8.79 | 10.35 | 5.80 | 0.57 | 1.32 | 2.91 | 10.79 |

Based on the table above, for compositions that comprise 5 wt % of the surfactant system at pH value of 5.5 and with a weight ratio of the APG to the acyl glutamate from 0.1, all of these compositions have foam creaminess values and foam stability values that are acceptable (Examples 16 to 19). Preferred compositions in terms of foam creaminess is Example 16, in which the foam creaminess value is less than 1500. Preferred compositions in terms of foam stability are Examples 16 and 17, in which the foam stability value is less than 5 and less than 7, respectively.

For compositions that comprise 20 wt % of the surfactant system at pH value of 5.5 and with a weight ratio of the APG to the acyl glutamate from 0.1, all of these compositions also have foam creaminess values and foam stability values that are acceptable (Examples 22 to 25). Preferred compositions in terms of foam stability are Examples 22 to 24, in which the foam stability value is less than 5.

The composition that comprises 10 wt % of the surfactant system at pH value of 5.5 with a weight ratio of the APG to the acyl glutamate that is 1, is a preferred composition in terms of foam creaminess, in which the foam creaminess value is less than 1500 (Example 20).

compositions also have foam creaminess values and foam stability values that are acceptable (Examples 31, 33 to 36). Preferred compositions in terms of foam creaminess are Examples 31 and 33, in which the foam creaminess value is less than 1500. Preferred compositions in terms of foam stability are Examples 31, 33 to 35, in which the foam stability value is less than 5.

In summary, based on Tables 10 to 13 above, all the compositions have a foam creaminess value of less than 2000 and a foam stability value of less than 11, which are acceptable.

Cytosensor Microphysiometer Assay

The Cytosensor Microphysiometer Assay ("CMA") is a known in vitro cellular toxicity test used to evaluate ocular irritancy. A microphysiometer is used to detect and monitor the extracellular changes in pH in L929 (mouse fibroblast) cells after exposure to a test material. Changes in the pH are caused by variations in the metabolic rate, measured indirectly as a function of changes in extracellular acidification. Metabolic rates after each test material concentration (dose) are measured and compared to baseline values. A percent of control metabolic rate is determined for each dose, and that

TABLE 13

| Ingredients (wt %)/Value of Foam Creaminess and Foam Stability | Ex. 26 | Ex. 27 | Ex. 28 | Ex. 29 | Ex. 30 | Ex. 31 | Ex. 33 | Ex. 34 | Ex. 35 | Ex. 36 |
|---|---|---|---|---|---|---|---|---|---|---|
| Decyl Glucoside (A) | 0.5% | 1.5% | 2.5% | 3.5% | 4.5% | 14.0% | 6.0% | 10.0% | 14.0% | 18.0% |
| Sodium Cocoyl Glutamate (B) | 4.5% | 3.5% | 2.5% | 1.5% | 0.5% | 6.0% | 14.0% | 10.0% | 6.0% | 2.0% |
| Total Surfactant (A + B) | 5.0% | 5.0% | 5.0% | 5.0% | 5.0% | 20.0% | 20.0% | 20.0% | 20.0% | 20.0% |
| Weight Ratio of A:B | 0.11 | 0.43 | 1.00 | 2.33 | 9.00 | 2.33 | 0.43 | 1.00 | 2.33 | 9.00 |
| pH value | 7.0 | 7.0 | 7.0 | 7.0 | 7.0 | 6.0 | 7.0 | 7.0 | 7.0 | 7.0 |
| Foam Creaminess Value | 1659 | 1569 | 1559 | 1758 | 1820 | 1394 | 1404 | 1663 | 1759 | 1739 |
| Foam Stability Value | −0.44 | −1.20 | −1.14 | 8.37 | 8.44 | −0.76 | −2.52 | 2.21 | 4.55 | 9.45 |

Based on the table above, for compositions that comprise 5 wt % of the surfactant system at pH value of 7.0 and with a weight ratio of the APG to the acyl glutamate from 0.1, all of these compositions have foam creaminess values and foam stability values that are acceptable (Examples 26 to 30). Preferred compositions in terms of foam stability are Examples 26 to 28, in which the foam stability value is less than 5.

For compositions that comprise 20 wt % of the surfactant system at pH value of 6.0 or 7.0 and with a weight ratio of the APG to the acyl glutamate from 0.1, all of these value is plotted on a dose response curve to determine a $MRD_{50}$ value (mg/mL). The higher the $MRD_{50}$ value (mg/mL), the lower the ocular irritancy of the test material.

Exemplary rinse-off cleansing compositions for the present invention are provided in Table 14 below. These exemplary rinse-off cleansing compositions are prepared by traditional means known to those of ordinary skill in the art by mixing the following ingredients. After the test samples are prepared, they are sent to the Institute for In Vitro Sciences ("IIVS") and the CMA is performed by the IIVS. Specific CMA procedures can be found at the following IIVS website (http://iivs.org/testing-services/assays/ocular/cytosensor-microphysiometer/).

(mg/mL) of 2.29 (Example 38) (Ratio of $MRD_{50}$ value to Control is 0.088). This shows that adding CAPB at 50% of the total surfactant level causes higher ocular irritancy.

TABLE 14

| Ingredients (wt %) | Ex. 37 (Control) | Ex. 38 | Ex. 39 (Control) | Ex. 40 | Ex. 41 | Ex. 42 (Control) | Ex. 43 | Ex. 44 | Ex. 45 (Control) | Ex. 46 |
|---|---|---|---|---|---|---|---|---|---|---|
| Disodium Cocoyl Glutamate[1] | 10.00 | 5.00 | 10.00 | 8.00 | 8.00 | 10.00 | 8.00 | 8.00 | — | — |
| Decyl Glucoside[2] | — | — | — | — | — | — | 2.00 | — | 5.00 | 5.00 |
| Cocamidopropyl betaine[3] (CAPB) | — | 5.00 | — | — | — | — | — | — | — | — |
| Cocamidopropyl Hydroxysultaine[4] (Sult) | — | — | — | — | 2.00 | — | — | 2.00 | — | 2.00 |
| Sodium Lauroamphoacetate[5] (NaLAA) | — | — | — | 2.00 | — | — | — | — | — | — |
| Preservative | 0.60 | 0.60 | 0.60 | 0.60 | 0.60 | 1.35 | 1.35 | 1.35 | 1.35 | 1.35 |
| Glycerine | — | — | — | — | — | — | — | — | 10.00 | 10.00 |
| Antibacterial Active | 0.05 | 0.05 | 0.05 | 0.05 | 0.05 | 0.05 | 0.05 | 0.05 | 0.05 | 0.05 |
| Perfume | — | — | 0.2 | 0.2 | 0.2 | 0.2 | 0.2 | 0.2 | 0.3 | 0.3 |
| Citric acid | | | | | Adjust to target pH | | | | | |
| Water | | | | | Q.S. | | | | | |
| pH | 6.3 | 6.4 | 5.5 | 5.5 | 5.5 | 5.5 | 5.6 | 5.6 | 6.0 | 7.0 |

[1]Available from Ajinomoto (e.g. Amisoft ® ECS-22W) or BASF (e.g. Plantapon ® ACG HC).
[2]Available from BASF (e.g. Plantacare ® 2000UP) or Dow Chemical (e.g. Ecosense ™ 3000).
[3]Available from BASF (e.g. Plantacare ® K 55) or Lubrizol (e.g. Schercotaine ™ CAB-35) or Solvay (Mackam ™ DH-13).
[4]Available from Solvay (e.g. Mackam ™ 50SB) or Lubrizol (e.g. Schercotaine ™ SCAB-50).
[5]Available from BASF (e.g. Dehyton ® ML) or Solvey (e.g. Miranol ® Ultra L32).

Comparative Test to Show Impact of Surfactants Added at Different Amounts on Ocular Irritancy The ocular irritancy of each of the test samples (Examples 37 to 44) is measured by IIVS using the CMA as described above, and the results are shown in Table 15 hereinafter. The higher the $MRD_{50}$ value (mg/mL), the lower the ocular irritancy of the test sample.

TABLE 15

| Ingredients (wt %)/ $MRD_{50}$ value (mg/mL) | Ex. 37 (Control) | Ex. 38 | Ex. 39 (Control) | Ex. 40 | Ex. 41 | Ex. 42 (Control) | Ex. 43 | Ex. 44 | Ex. 45 (Control) | Ex. 46 |
|---|---|---|---|---|---|---|---|---|---|---|
| Disodium Cocoyl Glutamate | 10.00 | 5.00 | 10.00 | 8.00 | 8.00 | 10.00 | 8.00 | 8.00 | — | — |
| Decyl Glucoside | — | — | — | — | — | — | 2.00 | — | 5.00 | 5.00 |
| Cocamidopropyl betaine (CAPB) | — | 5.00 | — | — | — | — | — | — | — | — |
| Cocamidopropyl Hydroxysultaine (Sult) | — | — | — | — | 2.00 | — | — | 2.00 | — | 2.00 |
| Sodium Lauroamphoacetate (NaLAA) | — | — | — | 2.00 | — | — | — | — | — | 2.00 |
| IIVS Test Number | Test 1 | Test 1 | Test 2 | Test 2 | Test 2 | Test 3 | Test 3 | Test 3 | Test 4 | Test 4 |
| $MRD_{50}$ value (mg/mL) | 26.00 | 2.29 | 9.18 | 5.98 | 8.06 | 7.70 | 8.51 | 5.48 | 13.8 | 8.76 |
| Ratio of $MRD_{50}$ value/Control | 1.00 (Control) | 0.088 | 1.00 (Control) | 0.65 | 0.87 | 1.00 (Control) | 1.11 | 0.71 | 1.00 (Control) | 0.63 |

IIVS Test 1

Based on the table above, a composition with the acyl glutamate (e.g. disodium cocoyl glutamate) making up 100% of the total surfactant level gives a $MRD_{50}$ value (mg/mL) of 26.00 (Example 37—Control), as compared to a composition with the acyl glutamate making up 50% of the total surfactant level and CAPB making up 50% of the total surfactant level (i.e. weight ratio of acyl glutamate to CAPB is 1.0) which gives a significantly lower $MRD_{50}$ value IIVS Test 2

A composition with the acyl glutamate making up 80% of the total surfactant level and NaLAA making up 20% of the total surfactant level (i.e. weight ratio of acyl glutamate to NaLAA is 4.0) (Example 40) slightly reduces the $MRD_{50}$ value (mg/mL) from 9.18 to 5.98 when compared to the Control Example 39 (Ratio of $MRD_{50}$ value to Control is 0.65).

A composition with the acyl glutamate making up 80% of the total surfactant level and Sult making up 20% of the total surfactant level (i.e. weight ratio of acyl glutamate to Sult is 4.0) (Example 41) similarly reduces the $MRD_{50}$ value (mg/mL) slightly from 9.18 to 8.06 when compared to the Control Example 39 (Ratio of $MRD_{50}$ value to Control is 0.87). This shows that adding NaLAA or Sult at 20% of the total surfactant level does not have a significant negative impact ocular irritancy.

IIVS Test 3

A composition with the acyl glutamate making up 80% of the total surfactant level and the APG (e.g. decyl glucoside) making up 20% of the total surfactant level (i.e. weight ratio of the APG to the acyl glutamate is 0.23) (Example 43) slightly increases the $MRD_{50}$ value (mg/mL) from 7.7 to 8.51 when compared to the Control Example 42 (Ratio of $MRD_{50}$ value to Control is 1.10). This shows that adding the APG at 20% of the total surfactant level helps to lower ocular irritancy. It is believed, without being limited by theory, that as the weight ratio of the APG to the acyl glutamate increases, the ocular irritancy may be reduced.

A composition with the acyl glutamate making up 80% of the total surfactant level and Sult making up 20% of the total surfactant level (i.e. weight ratio of acyl glutamate to Sult is 4.0) (Example 44) slightly reduces the $MRD_{50}$ value (mg/mL) from 7.7 to 5.48 when compared to the Control Example 42 (Ratio of $MRD_{50}$ value to Control is 0.71). This shows that adding Sult at 20% of the total surfactant level does not significantly impact ocular irritancy.

IIVS Test 4

A composition with the APG making up 100% of the total surfactant level gives a $MRD_{50}$ value (mg/mL) of 13.8 (Example 45—Control), as compared to a composition with the APG making up 71.43% of the total surfactant level and NaLAA making up the remaining 28.57% of the total surfactant level (i.e. weight ratio of the APG to NaLAA is 2.5) which gives a slightly lower $MRD_{50}$ value (mg/mL) of 8.76 (Example 46) (Ratio of $MRD_{50}$ value to Control is 0.63). This shows that adding NaLAA at 28.57% of the total surfactant level does not significantly impact ocular irritancy.

Exemplary Rinse-Off Cleansing Compositions

The following rinse-off cleansing compositions (finished formulations) are prepared by traditional means known to those of ordinary skill in the art by mixing the following ingredients.

TABLE 16

| Ingredients (wt %) | A | B | C | D | E | F | G | H |
|---|---|---|---|---|---|---|---|---|
| Disodium Cocoyl Glutamate[1] | 1.5 | — | — | — | 14.0 | 7.5 | 12.6 | 12.0 |
| Sodium Cocoyl Glutamante[2] | — | 10.5 | — | — | — | — | — | — |
| Sodium Lauroyl Glutamate[3] | — | — | 5.0 | — | — | — | — | — |
| Sodium Myristoyl Glutamate[4] | — | — | — | 3.0 | — | — | — | — |
| Decyl Glucoside[5] | 3.5 | — | — | — | 6.0 | — | — | 28 |
| Cocoyl Glucoside[6] | — | 4.5 | — | — | — | — | 5.4 | — |
| Lauryl Glucoside[7] | — | — | 5.0 | — | — | 7.5 | — | — |
| Capryly/Capryl Glucoside[8] | — | — | — | 7.0 | — | — | — | — |
| Glycerine | — | 1.0 | — | — | 2.0 | 2.0 | 1.0 | 1.0 |
| Sodium Lauroamphoacetate[9] | — | — | — | — | — | 2.0 | — | — |
| Sodium chloride | — | — | — | — | 1.0 | 1.0 | 1.5 | — |
| Xanthan Gum | — | — | — | — | — | — | 1.0 | — |
| PEG-150 Distearate[10] | — | — | — | — | 1.0 | — | — | — |
| PEG-120 Methyl Glucose Trioleate[11] | — | — | — | — | — | 2.0 | — | — |
| Antibacterial Agent | 0.05 | 0.20 | 0.10 | 0.05 | 0.30 | 0.20 | 0.30 | 0.30 |
| Perfume | 0.5 | 0.5 | 0.1 | 0.8 | 1 | 1 | — | 1.5 |
| Citric acid | Adjust to target pH | | | | | | | |
| Preservative | Q.S. | | | | | | | |
| Water | Q.S. | | | | | | | |
| pH | 4 | 5.5 | 4.5 | 4.5 | 5.5 | 5.5 | 5 | 6 |

[1]Available from Ajinomoto (e.g. Amisoft ® ECS-22W) or BASF (e.g. Plantapon ® ACG HC).
[2]Available from Ajinomoto (e.g. Amisoft ® CS-11).
[3]Available from Ajinomoto (e.g. Amisoft ® LS-11).
[4]Available from Ajinomoto (e.g. Amisoft ® MS-11).
[5]Available from BASF (e.g. Plantacare ® 2000UP) or Dow Chemical (e.g. Ecosense ™ 3000).
[6]Available from BASF (e.g. Plantacare ® 818UP) or Dow Chemical (e.g. Ecosense ™ 919).
[7]Available from BASF (e.g. Plantacare ® 1200UP) or Dow Chemical (e.g. Ecosense ™ 1200).
[8]Available from BASF (e.g. Plantacare ® 810UP).
[9]Available from BASF (e.g. Dehyton ® ML) or Solvey (e.g. Miranol ® Ultra L32).
[10]Available from Evonik (e.g. REWOPAL ® PEG 6000 DS) or BASF (e.g. Eumulgin ® EO 33).
[11]Available from Lubrizol (e.g. Glucamate ™ LT).

It will be understood that reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm" All numeric ranges described herein are inclusive of narrower ranges; delineated upper and lower range limits are interchangeable to create further ranges not explicitly delineated. Embodiments described herein can comprise, consist essentially of, or consist of, the essential components as well as optional pieces described herein. As used in the description and the appended claims, the singular forms "a," "an," and "the" are intended to include the plural forms as well, unless the context clearly indicates otherwise.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A rinse-off cleansing composition consisting of:
   from about 5% to about 15%, by total weight of said cleansing composition, of a surfactant system consisting of an alkyl polyglycoside and an acyl glutamate;
   optionally fragrances perfumes, preservatives, and/or antibacterial actives;
   wherein the weight ratio of the alkyl polyglycoside to the acyl glutamate is from about 2 to about 9; wherein pH value of said cleansing composition is 7.5 or less.

2. The rinse-off cleansing composition according to claim 1, wherein the pH value of said cleansing composition is no more than 7.0.

3. The rinse-off cleansing composition according to claim 1, wherein said cleansing composition has a pH value from about 5 to about 5.5.

4. The rinse-off cleansing composition according to claim 1, wherein said cleansing composition has a pH value of greater than 5.5 to 7.5.

5. The rinse-off cleansing composition according to claim 1, wherein said cleansing composition has a pH value of from about 3.5 to about 4.5.

6. The rinse-off cleansing composition according to claim 1, wherein the acyl glutamate is C10-C14 acyl glutamate.

7. A rinse-off cleansing composition, consisting of:
   from about 5% to about 15%, by total weight of said cleansing composition, of a surfactant system, consisting of an alkyl polyglycoside and an acyl glutamate, wherein the weight ratio of the alkyl polyglycoside to the acyl glutamate is greater than 1, and
   optionally fragrances perfumes, preservatives, and/or antibacterial actives;
   wherein pH value of said cleansing composition is from 5 to 6.

8. A rinse-off skin cleansing composition consisting of:
   from about 5% to about 15%, by weight of the cleansing composition, of a surfactant system consisting of:
   a. an alkyl polyglycoside comprising decyl glucoside;
   b. an acyl glutamate selected from the group consisting of sodium cocoyl glutamate, disodium cocoyl glutamate, and combinations thereof;
   wherein the weight ratio of alkyl polyglycoside to acyl glutamate is from about 1.5 to about 2;
   optionally fragrances perfumes, preservatives, and/or antibacterial actives;
   wherein the composition has a pH value of from about 3.5 to about 4.5.

9. The rinse-off cleansing composition of claim 8, wherein the weight ratio of alkyl polyglycoside to acyl glutamate is about 2.

10. The rinse-off cleansing composition of claim 8, wherein the surfactant system is present in an amount from about 7% to about 12% by weight of the cleansing composition.

11. The rinse-off cleansing composition of claim 8, wherein the surfactant system is present in an amount from about 8% to about 10% by weight of the cleansing composition.

12. The rinse-off cleansing composition of claim 8, wherein the composition has a pH value of from about 4 to about 4.5.

* * * * *